United States Patent [19]

Azuma et al.

[11] Patent Number: 4,565,626

[45] Date of Patent: Jan. 21, 1986

[54] APPARATUS FOR BLOOD TREATMENT BY PRESSING BLOOD INTO TREATING MATERIAL AND THEN DRAWING IT OUT

[75] Inventors: Junichi Azuma, Nishinomiya; Koichi Watanabe, Kawabe; Masatake Hori, Itami, all of Japan

[73] Assignee: Takeda Chemical Industries, Ltd., Osaka, Japan

[21] Appl. No.: 557,227

[22] Filed: Nov. 30, 1983

[51] Int. Cl.⁴ .............................................. B01D 31/00
[52] U.S. Cl. .................................... 210/138; 210/196; 210/321.1; 210/433.2
[58] Field of Search ................... 210/138, 257.2, 321.1, 210/321.3, 433.2, 196, 927

[56] References Cited

U.S. PATENT DOCUMENTS

| | | | |
|---|---|---|---|
| 3,493,496 | 2/1970 | Bray et al. | 210/257.2 X |
| 3,849,305 | 11/1974 | Manjikian | 210/138 X |
| 3,864,248 | 2/1975 | Granger et al. | 210/321.3 X |
| 4,013,564 | 3/1977 | Nose | 210/434 |
| 4,096,059 | 6/1978 | Pinkerton | 210/321.3 X |

FOREIGN PATENT DOCUMENTS

WO80/02805 12/1980 PCT Int'Appl. .

OTHER PUBLICATIONS

Artificial Organs, vol. 9, No. 2 (Plasma Perfusion with Porous Blood Channels), pp. 506–509, T. Suehiro et al., 9/2/1980.

Primary Examiner—David Sadowski
Attorney, Agent, or Firm—Wenderoth, Lind & Ponack

[57] ABSTRACT

An apparatus for blood treatment has a housing having a blood inlet for introducing the blood to be treated and a blood outlet for exhausting the treated blood, at least one blood channel within the housing and extending from the inlet to the outlet and being constituted by a plasma-separating membrane capable of allowing the plasma component of blood to permeate therethrough while preventing the blood cells from penetrating therethrough. A blood treating material is packed in the space within the housing around the blood channel. A pump is connected to the inlet for pumping blood into the inlet. A pressure varying mechanism operatively associated with the housing imposes from outside the housing on the space within the housing pressure changes for alternately changing the direction of the pressure difference between the inside of the blood channel and the blood treating material-containing space, so that the plasma component of the blood flow in the blood channel is caused to permeate through the plasma-separating membrane toward the blood treating material to bring the plasma into contact with the blood treating material, and the plasma is thereafter caused to be returned to the blood channel through the plasma-separating membrane.

7 Claims, 20 Drawing Figures

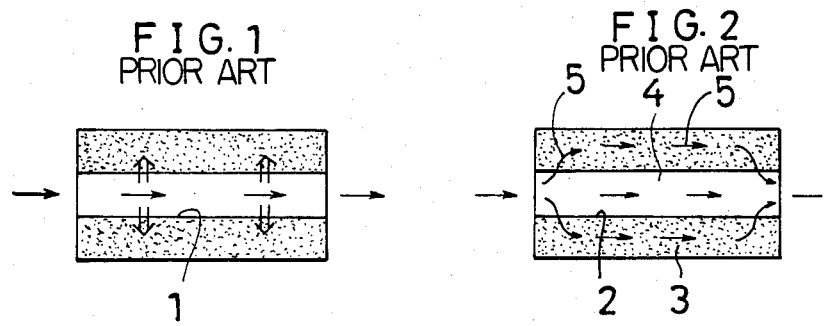
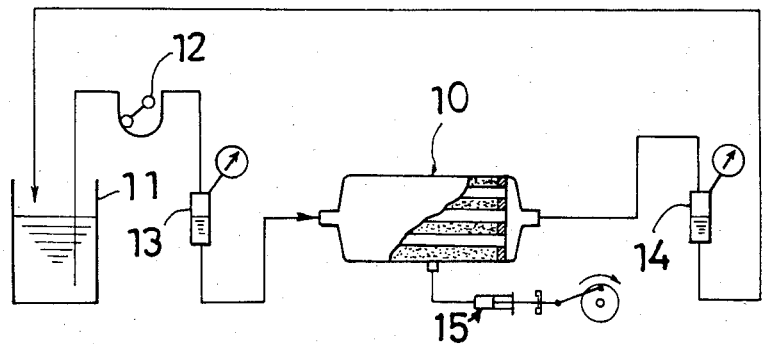
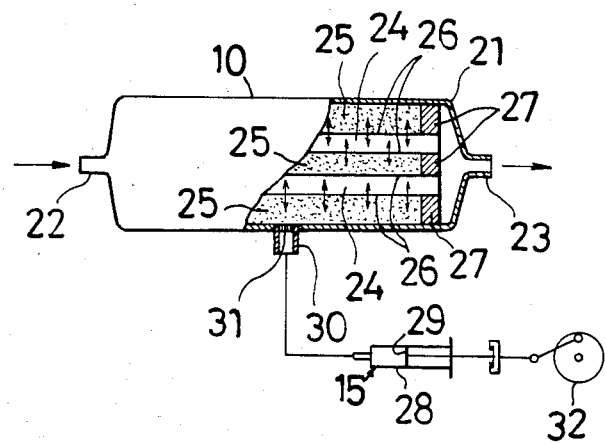

APPARATUS FOR BLOOD TREATMENT BY PRESSING BLOOD INTO TREATING MATERIAL AND THEN DRAWING IT OUT

BACKGROUND OF THE INVENTION

1. Field of the Invention

The present invention relates to an apparatus for treatment of blood and more particularly to an apparatus for removing undesirable substances from blood plasma, and in which only the plasma is separated from a blood stream by a plasma separating membrane which prohibits the penetration of blood cellular components but allows the plasma to pass therethrough. In the apparatus the plasma is, after the removal of the undesirable substances, returned to the blood stream again through said plasma separating membrane.

2. Description of the Prior Art

Three methods of treating blood by the use of a blood treating material have been reported:

1. A direct hemoperfusion method (hereinafter called the "DHP method");
2. A plasma perfusion method (hereinafter called the "PP method"); and
3. A method of practicing the PP method by using a membrane-type plasma separator filled with a blood treating material (hereinafter called the "CPP method"). An example is described in U.S. Pat. No. 4,013,564, and in Jinko Zoki, Vol. 9, No. 2, pp 506–509.

Of these methods, the DHP method has already been put in practice commercially. However this method, in which the blood is brought into direct contact with the blood treating material, has disadvantages, such as that it causes a decrease in blood platelets and white blood cells in the perfused blood, thrombogenesis, hemolysis, and microparticles of the blood treating material are sometimes released into the blood being treated. One countermeasure to these disadvantges is to coat the blood treating material with a substance which is highly biocompatible with the blood. However, in the present state of the technology, the use of such a coating is inevitably accompanied by a lowering of efficiency and an increase in the complexity of the process of manufacturing the blood treating material.

The PP method in which the blood itself is not brought into direct contact with the blood treating material, is free from such degeneration of the blood cellular components described above, but the apparatus, including the blood circuit, is complicated because this method requires a separate pump in the plasma circuit and a filter through which the treated plasma is returned to the blood stream. In addition, it is a further disadvantage of this method that a larger volume of extracorporeal circulating blood is required.

The CPP method not only is free from the problem of the direct contact between the blood and the blood treating material but also has an advantage that the problem of microparticles of the blood treating material being released into the blood is eliminated because the plasma separating membrane functions as a microfilter. Therefore, consideration has been given to putting this method into practice in two ways using either a hollow fiber membrane or a flat membrane. One way is to remove the undesired solutes by dispersing them through a so-called dialysing membrane 1, as shown schematically in FIG. 1. The other way is to treat the plasma with a blood treating material, as is shown in FIG. 2, causing only the plasma component 5 to separate from a blood stream path 4 through a high-flux membrane 2 which separates blood treating material 3 from the blood stream, flow through the blood treating material 3, and then return to the blood stream. However, the former way, which is really outside the scope of the PP method, is not suitable for treating substances having a molecular weight higher than a medium value, while the latter way can hardly be expected to work effectively, if carried out in the way described, because the plasma permeation rate through the membrane is not constant and stable, but depends on the pressure resistance in the blood stream path 4 and the permeability of the membrane 2. Furthermore, the entire stream of the plasma has such a simple flow pattern that the plasma flows toward the blood treating material 3 in the vicinity of the blood stream entrance and returns to the original blood stream path 4 in the vicinity of the blood stream exit 4, as is indicated by arrows 5 in FIG. 2, so that only about half the area of the membrane 2 carries out filtration in the vicinity of the entrance and the remaining half is used for the return of the treated plasma to the blood stream. Accordingly, in the region of the entrance of the blood stream path 4 there is formed a protein gel layer, which causes a substantial decrease of the effective area of the membrane 2, producing a serious disadvantage that a stable flow of blood is disturbed.

OBJECTS AND SUMMARY OF THE INVENTION

The principal object of the present invention is to provide an improved and highly effective apparatus for blood treatment, in which the direction of the pressure difference across the plasma separating membrane is alternately forcibly changed by a simple externally provided means such as a piston pump or a clamp, so as to effectively contact the plasma with the blood treating material.

Another object of the present invention is to provide an improved apparatus, in which the direction of the pressure difference across the plasma separating membrane is alternately forcibly changed to prevent the formation of a protein gel layer or the clogging of the pores of the membrane so as to cause the membrane to carry out stable filtration for a long time.

For the achievement of the above objects the present invention provides an apparatus comprising a blood treating unit, a pressure-varying means and a blood pump. The blood treating unit consists of a plurality of blood stream channels made of a plasma-separating porous membrane and of a blood treating material packed around the blood stream channels, both the blood stream channels and the blood treating material being encased in a housing having a blood inlet port and a blood outlet port. The blood to be treated, which is fed by the blood pump to the blood treating unit through the blood inlet, flows through the blood stream channels in the unit. While the blood is flowing through the channels, the pressure-varying mean alternately changes the direction of the pressure difference between the space where the blood treating material is packed and the blood stream channels so as to cause the plasma component in the blood to permeate the plasma-separating membranes which form the blood stream channels reciprocally between the blood stream channels and the blood treating material. In such a manner, the plasma is cleaned by being brought into contact with the blood treating material, by adsorption or chemical or biological reaction with the blood treating material, and then caused to flow forcibly back into the blood stream channels.

In the apparatus of the present invention, said pressure-varying means can be either an external mechanical device which alternately raises and reduces the pressure in the space where the blood treating material is packed, or as a clamp operating on the external blood flow circuit connected with the outlet port of the blood treating unit.

BRIEF DESCRIPTION OF THE DRAWINGS

The present invention will be described in greater detail in connection with the accompanying drawings in which:

FIGS. 1 and 2 are schematic views showing examples of blood treating units of the prior art.

FIG. 3 is a diagrammatic view of an example of a blood treating apparatus according to the present invention, wherein the blood treating unit is shown partially in cross-section;

FIG. 4 is a partially cross-sectioned view on a larger scale of the blood treating unit of FIG. 3;

DETAILED DESCRIPTION OF THE INVENTION

Figure 5:
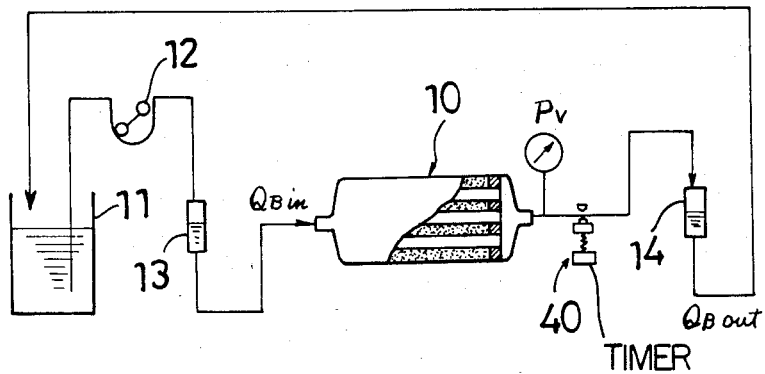
FIG. 5 is a view similar to FIG. 3 showing another example of the blood treating apparatus according to the present invention.

FIG. 3 shows a blood treating apparatus in which the blood treating unit according to the present invention is used. The apparatus has a blood tank 11, a blood pump 12 connected to tank 11, a bubble trap 13, the blood treating unit 10, including pressure-varying means 15 and a further bubble trap 14 connected in series. The blood to be treated is fed by the blood pump 12 from the blood tank 11 to the blood treating unit 10 through the bubble trap 13. The blood fed to the blood treating unit 10 is cleaned there while passing therethrough, and is then returned to the blood tank 11 through the bubble trap 14. The blood tank may well be a human body.

The details of the first embodiment of the blood treating unit 10 used in the apparatus of FIG. 3 are shown in FIG. 4, together with an embodiment of the pressure-varying means 15 forming a part thereof. This embodiment of the blood treating unit comprises a housing 21 having a blood inlet port means 22, a blood outlet port means 23 and a pressure-introducing port 30. A known blood treating material is contained within the housing 25 and a plurality of blood channels 24 is embedded in the blood treating material 25 extending from the inlet port means to the outlet port means. Each of the blood channels 24 is made of a tubular plasma-separating porous membrane 26 of a known material suitable for this purpose. The respective ends of each blood stream channel 24 are open to the blood inlet port means 22 and the blood outlet port means 23, and the blood treating material 25 adjacent to the port means is contained within the housing 21 by means of a wall 27 at the outlet side and a corresponding wall, not visible in the drawing, at the inlet side, so the material 25 is prevented from being mixed into the blood stream. The pressure-introducing port 30 opens into the blood treating material containing space around the channel 24 and is connected with the pressure-varying means which in this embodiment is a mechanical means in the form of a pump having a cylinder 28 and a piston 29 reciprocally movable therein by a piston driving mechanism 32, and a pressure-transmitting medium in the cylinder 28 is alternately pumped toward and drawn away from the blood treating material 25. A filter 31 is provided in the port 30. The pressure-transmitting medium can be physiological saline. The piston-driving mechanism 32 can be any known mechanism to drive a piston reciprocally.

In the thus constituted blood treating unit, the blood being transferred from a patient (corresponding to the blood tank 11 in FIG. 3) is introduced into the blood treating unit via the inlet port means 22. As the blood introduced is passing through the blood channels 24, the piston 29 carries out more than one cycle of reciprocal movement to alternate the direction of the pressure difference between the blood channels 24 and the space containing the blood treating material 25 so as to cause the plasma component of the blood to permeate the plasma-separating membranes 25 first in one direction and then in the opposite direction as shown by the arrows. A withdrawal motion of the piston 29, i.e. to the right in FIG. 4, effects a pressure decrease in the space where the blood treating material is packed to a pressure below the partial pressure of the plasma in the flowing blood, causing the plasma component of the blood in the blood channels 24 to be drawn into the blood treating material 25 through the whole area of the plasma-separating membranes 26. While the plasma thus drawn in is in contact with the blood treating material 25, the substances to be removed from the plasma are removed through the adsorption by, or the chemical or biological reaction with, the blood treating material 25. When the piston 29 is moved in the pressurizing direction, to the left in FIG. 4, the pressure in the space where the blood treating material 25 is packed is made higher than that of the plasma in the blood channels 24. The plasma, which is now cleaned, is consequently pushed back through the membranes toward the blood channels 24 through the whole area of the plasma-separating membrane 26 to join the blood stream again. While the blood is passing through the blood channels 24, the above-described plasma movement through the plasma-separating membranes 26 is repeated one to several times as the occasion demands. In the present embodiment of the blood treating unit, the blood channels 24 can be constituted as capillaries made of hollow fibers. In this case the hollow fibers themselves act as the plasma-separating membranes 26, with the hollow interiors thereof serving as the blood channels 24. A bundle of a larger number of hollow fibers with a blood treating material packed between the fibers in the bundle can be used as a blood treating module having a large number of blood stream channels and a large surface area of the plasma-separating membrane. The plasma-separating membrane 26 is a porous membrane with a pore size, in general, of from 0.2 to 2.0 μm to prevent the blood cellular components from passing therethrough. However, a membrane with a smaller pore size can be used depending on the particle size of the blood treating material 25. The blood treating material 25 can be selected from among various adsorbents, enzymes and other conventional blood treating materials, depending on the kind of substances to be removed from the blood being treated. The blood treating unit can be provided with a plurality of pressure-introducing ports 30 to make the plasma movement smoother.

FIG. 5 shows another blood treating apparatus, in which a clamp mechanism 40 is employed as the pressure-varying means of the blood treating unit. This apparatus, therefore, differs from that shown in FIG. 3 in being provided with a clamp mechanism 40 instead of the pressure-varying pump 15 in FIG. 3.

Figure 6:
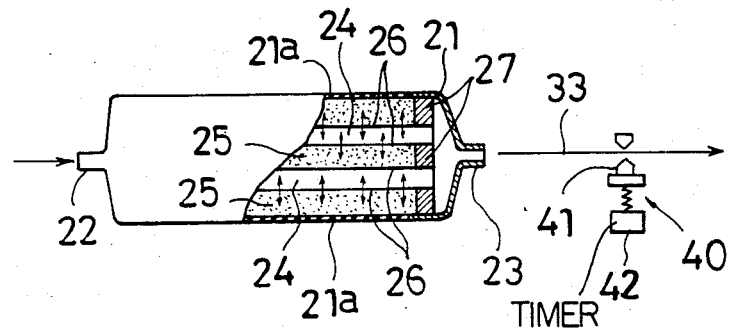
FIG. 6 is a view similar to FIG. 4 showing the blood treating unit and a clamp mechanism of FIG. 5.

The details of the blood treating unit and the clamp mechanism 40 in FIG. 5 are described with reference to FIG. 6. In FIG. 6, the housing 21 of the blood treating unit, the blood inlet port means 22 and the blood outlet port means 23, the blood treating material 25 and the plurality of blood channels 24 made of plasma-separating porous membranes, and the walls 27 are the same as described in connection with FIG. 4. The only differences are that there is no pressure introducing port, such as the port 30, and at least a part or the whole of the housing wall which is in direct contact with the blood treating material 25 is made of an elastic material 21a such as silicon rubber, butyl rubber or soft polyvinylchloride.

In the blood circuit 33 connected to the outlet port means 23 downstream of housing 21, there is provided a clamp mechanism 40 consisting of a throttle 41 and a timer 42 to actuate the throttle 41 intermittently. The throttle 41, which is for instance an electromagnetic valve, alternately restricts flow by partially closing or permits free flow by opening the circuit 33 at a predetermined time interval, being on-off controlled by the timer 42. The degree of throttling, which is freely adjustable, is preferably such as to cause in the circuit 33 a pressure $P_v$ which causes the plasma to permeate the plasma-separating membranes at the maximum filtration rate $Q_{Fmax}$ specific to the membranes. The circuit is not throttled completely, but it may be made to be completely throttled if a bypass is provided.

In this embodiment, the blood fed from a patient enters the housing 21 through the blood inlet port means 22, passes through the blood channels 24 constituted by the plasma-separating membranes 26 and returns to the patient through the circuit 33. In such a cyclic process of the blood flow, if the circuit 33 is throttled by the clamp mechanism 40, the pressure in the blood channels 24 is increased so that the plasma component flowing in the blood channels 24 is caused to permeate through the membranes 26 into the blood treating material 25 over the whole area of the plasma-separating membranes 26. In this case the pressure increase in the space in which the blood treating material 25 is packed is relieved by the expansion of the elastic material housing wall 21a so as to enable the plasma to flow continuously to the blood treating material-containing space. The plasma having filtered into the blood treating material-containing space comes into contact with the blood treating material 25 and is cleaned by adsorption or chemical or biological reaction. When the throttling of the circuit 33 discontinued, the restoring force of the elastic material 21a raises the pressure in the blood treating material-containing space sufficiently to cause the cleaned plasma to permeate back into the blood channels 24 again through the whole area of the plasma-separating membranes 26, so that the cleaned plasma joins the blood stream in the blood channels 24. While the blood is passing through the blood channels 24, the above-described plasma movement between the blood channels 24 and the blood treating material-containing space is repeated one to several times as the occasion demands. For instance, the number of repetitions is determined according to the restoring force of the elastic wall 21a of the housing. The elastic wall and the clamp mechanism together constitute the pressure varying means.

Figure 7:
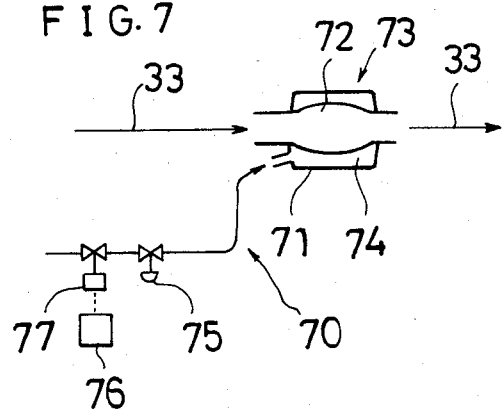
FIG. 7 is a schematic view showing a modified form of the clamp mechanism shown in FIG. 6.

FIG. 7 shows another embodiment 70 of the clamp mechanism. The clamp mechanism is constituted by a clamp unit 73 consisting of a soft inner tube 72 and a rigid outer case 71, which clamp unit is connected in the blood circuit 33. The rigid case 71 is provided with an air inlet port through which compressed air having the pressure controlled by a further valve 75 can be introduced into the space left around that inner tube 72 in the rigid outer case 71 to pinch the soft inner tube 72. A timer 76 and an electromagnetic valve 77 control the time and frequency of introduction of the compressed air and hence the pinching of the tube.

Figure 8:
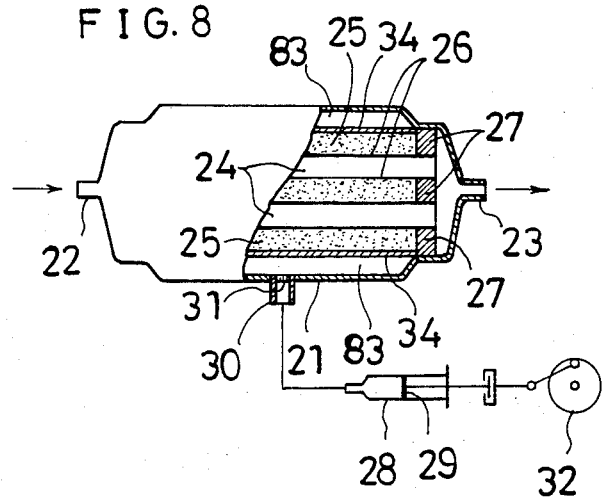
FIG. 8 is a view similar to FIG. 4 showing a modification of the embodiment of the blood treating unit of FIG. 4.

FIG. 8 shows a further embodiment of the blood treating unit. In this embodiment, a pressure space 83 is provided around the blood treating material 25 enclosed by an elastic enclosure 34 within the housing 21 and which is impermeable to plasma and to pressure transmitting medium. The pressure space 83 is filled with a pressure-transmitting medium supplied through the pressure-introducing port 30 which is connected to the cylinder 28 of the external pressure-varying pump like that shown in FIG. 4. A withdrawal motion of the piston 29 of the pressure-varying pump draws the pressure-transmitting medium out of space 83 effecting a pressure decrease in the pressure space 83. This pressure decrease is accompanied by a pressure decrease within the elastic enclosure 34 due to the expansion of the same. The pressure decrease within the elastic enclosure 34 causes the plasma component flowing in the blood channels 24 to filter through the plasma-separating membranes 26 into the space containing blood treating material 25. The blood treating material removes the waste contained in the plasma by adsorption or chemical or biological reaction. When the piston 29 moved in the pressurizing direction, the pressure-transmitting medium is forced into the pressure space 83, raising the pressure therein. The pressure increase in the pressure space 83 is transmitted through the elastic enclosure 34 to the space in which the blood treating material 25 is packed. The cleaned plasma is, therefore, caused to flow back into the blood channels 24 again through the whole area of the plasma-separating membranes 25. This embodiment has the advantage that any kind of liquid material can be used as the pressure-transmitting medium, because the blood treating material 25 is isolated from the pressure-transmitting material by means of the elastic enclosure 34.

Figure 9:
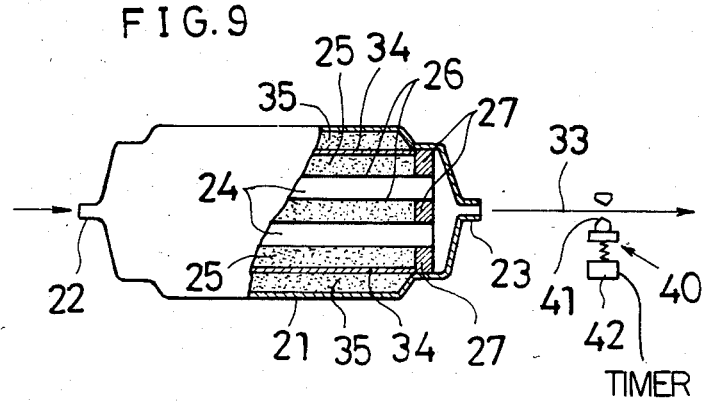
FIG. 9 is a view similar to FIG. 5 showing a modification of the embodiment of the blood treating unit of FIG. 5.

The idea of introducing a pressure-transmitting medium into the housing can also be supplied to an apparatus having a clamp mechanism such as is shown in FIG. 5. Such an embodiment is shown in FIG. 9. In this embodiment, an elastic material 35 is packed in the space formed between the housing 21 and the elastic enclosure 34 within the blood treating material 25 is contained. The reversible filtering of the plasma through the plasma-separating membranes 25 is effected by the throttling action of the clamp mechanism 40 and by the substantially reversible elasticity of both the elastic enclosure 34 and the elastic packing 35.

Figure 10:
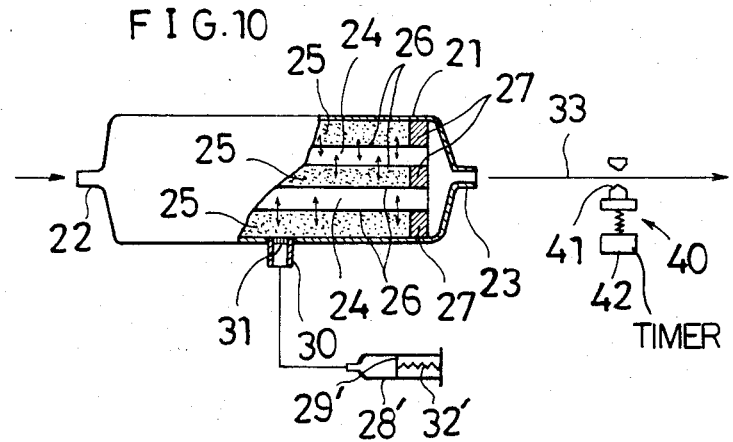
FIG. 10 is a view similar to FIG. 5 showing another modification of the blood treating unit shown in FIG. 5.

The embodiment shown in FIG. 10 is a modification of the embodiment shown in FIG. 6. This embodiment employs no elastic means in the housing 21, but employs an external piston mechanism consisting of a cylinder 28' and a piston 29' engaged by a spring 32' in the cylinder 28'. The cylinder 28' is connected with the housing 21 through the pressure-introducing port 30, enabling the plasma to flow through the filter 31 between the cylinder 28' and the space within which the blood treating material is packed. When the plasma filters through the plasma-separating membranes 26 into the blood treating material containing space at the time of the clamping action of the clamp mechanism 40, the plasma pushes the piston 29' to the right against the force of the spring 32' to accommodate the increased amount of plasma in the cleaning material containing space until the pressure of the plasma is balanced by the force of the spring. When the pressure in the blood channels 24 in reduced upon release of the clamping mechanism, the restoring force of the spring 32' which has been acting as means to counterbalance the pressure of the plasma, forces the plasma back to the blood channels 24. In this embodiment the spring 32' serves as the elastic means instead of the elastic packing or enclosure used in the embodiment shown in FIGS. 8 and 9. The spring 32' can be replaced with a compressible gas, such as air.

FIGS. 11 to 16, in which the housing 21, blood channels 24 and blood cleaning material 25 are shown schematically, show embodiments in which some attachments are incorporated.

Figure 11:
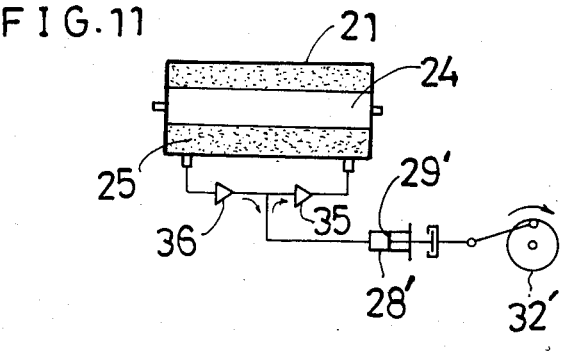
FIGS. 11 to 16 are diagrammatic views of modified forms of apparatus in which the blood treating unit of the present invention can be used.
Figure 12:
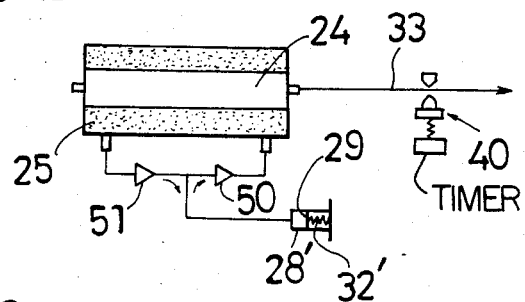

The embodiment shown in FIG. 11 employs separate pressure ports and two check valves 35 and 36 connected to make one the inlet pressure port and the other an outlet pressure port for the pressure-transmitting medium to flow in and out of the housing 21. The embodiment shown in FIG. 12 is a modification of the embodiment shown in FIG. 11, in which the pressure-varying pump is replaced with a clamp mechanism 40 and a pressure medium receiving spring loaded piston-cylinder mechanism 28', 29', 32' like that of FIG. 10.

Figure 13:
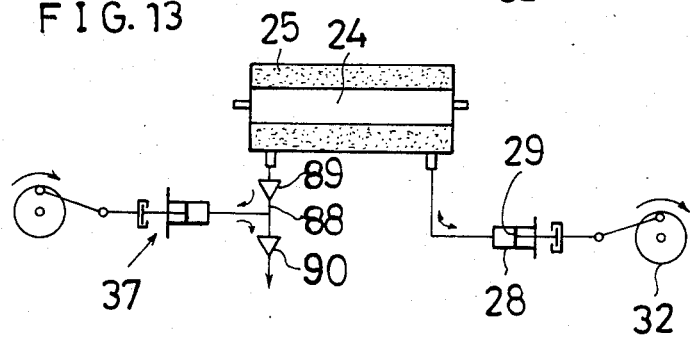
Figure 14:
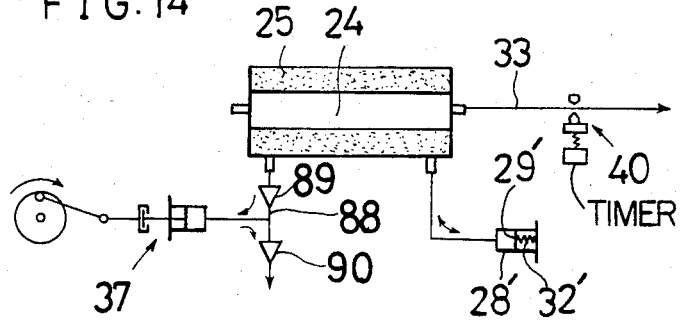

The embodiment shown in FIG. 13 is provided with a fluid removing means. The fluid contained in the plasma is quantitatively removed by means of an exhaust pipe 88 connected with the blood treatment material containing space in which the blood treating material 25 is packed, two check valves 89 and 90 and a piston pump 37 connected between the check valves. The embodiment shown in FIG. 14 is a modification of the embodiment shown in FIG. 13, in which the pressure-varying pump is replaced with a clamp mechanism 40 and a pressure medium receiving spring loaded piston-cylinder mechanism 28', 29', 32'.

Figure 15:
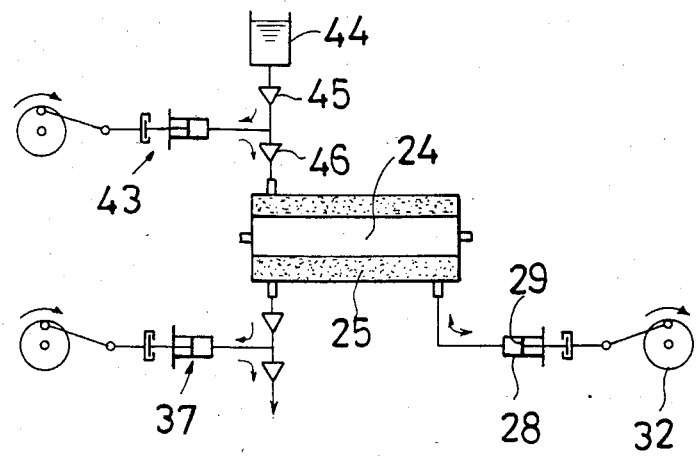
Figure 16:
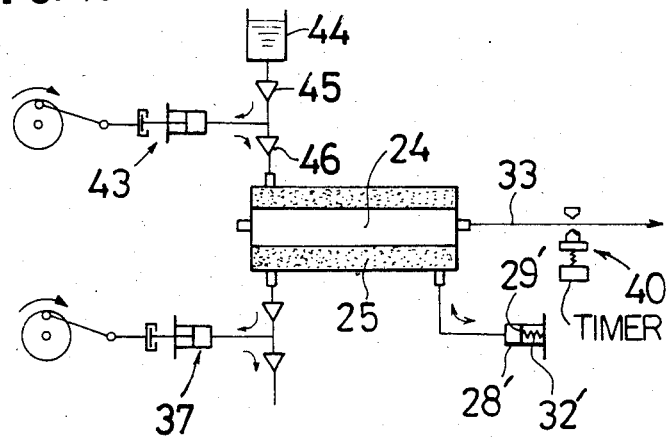

The embodiment shown in FIG. 15 is provided with a fluid substituting means, in addition to said fluid removing means. The fluid in a tank 44 is quantitatively supplied to the blood treating material 25 by means of two check valves 45, 46 and a piston pump 43 connected between the check valves. FIG. 16 shows a modification of the embodiment shown in FIG. 15 in which the pressure-varying pump is replaced by a clamp mechanism 40 and a pressure medium receiving spring loaded piston-cylinder mechanism 28', 29', 32'.

In some of the embodiments described above, a pressure-varying pump consisting of a piston and a cylinder is used as the pressure-varying means. However, the pressure-varying pump can of course be replaced with some other means, for instance, a roller pump which effects an increase and decrease in pressure according to the direction of its rotation.

EXPERIMENTAL RESULTS

The results of experiments with the apparatus according to the present invention will now be described.

A first experiment was conducted using the blood treating apparatus shown in FIGS. 3 and 4. The housing 21 of the blood treating unit 10 had an outer case of an SD-series artificial kidney manufactured by Takeda Chemical Industries with piping attached. The blood treating unit was constituted by a module consisting of said case, 2500 polypropylene hollow fibers (inner diameter: 330 $\mu$m max., pore diameter: 0.6 $\mu$m: manufactured by ENKA) as blood channels, and 50 gr of granular charcoal as a blood treating material. The effective total surface area of the blood channels, namely, the total surface area of the plasma-separating membranes was 0.5 $m^2$.

The blood used in the experiment was fresh bovine blood with a hematocrit value of 35%. In the blood, $VB_{12}$ and creatinine were supplied so that their concentrations were 20 mg/dl of plasma.

The experiment was carried out by circulating 2 liters of this blood in the blood apparatus shown in FIG. 3 for 2 hours at a blood flow rate $QB=100$ ml/min for causing the charcoal to perform adsorption and using a pressure-varying pump. For reference a similar experiment was also performed without using the pressure-varying pump.

Figure 17:
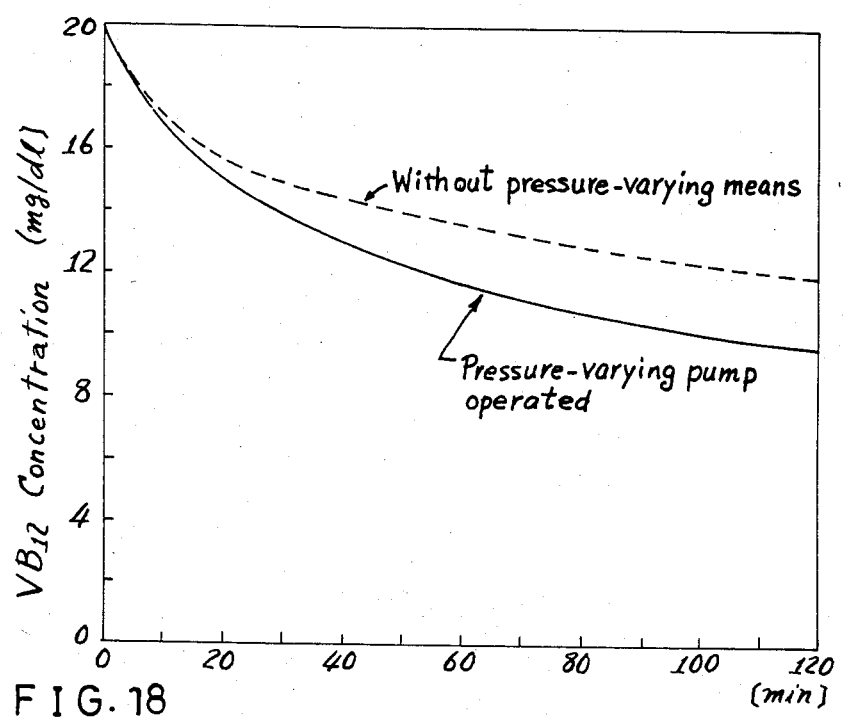
FIGS. 17 to 20 are graphs showing experimental results obtained by the use of the apparatus of the present invention.
Figure 18:
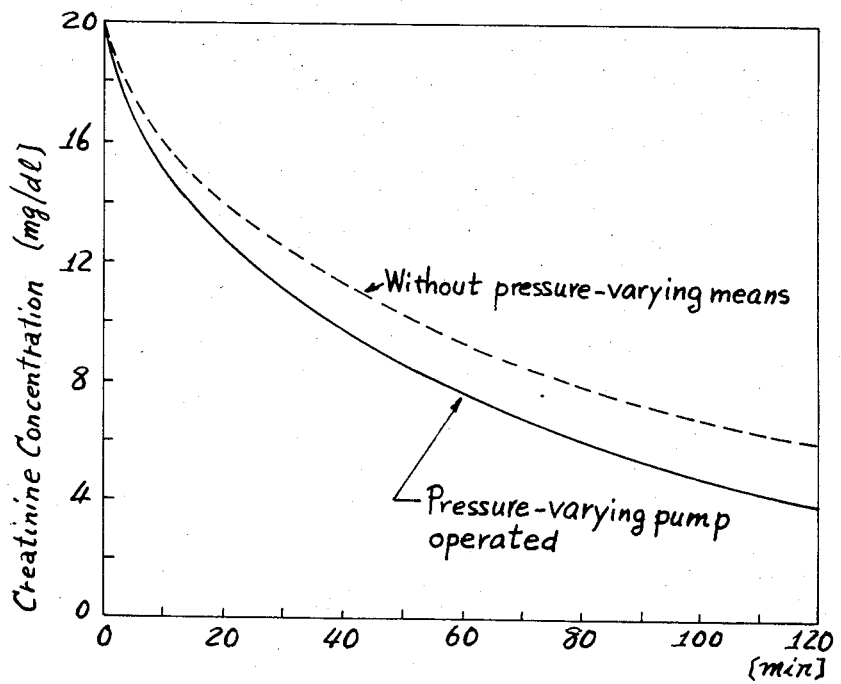

FIGS. 17 and 18 show the results for $VB_{12}$ and for creatinine, respectively. The solid lines in the Figures show the results of the first experiment, and the dotted lines those of the reference experiment in which a pressure-varying pump was not used. FIG. 17 shows that the $VB_{12}$ concentration decayed to 60% of its original value in 55 minutes (solid line), which is shorter than a half of the 120 minutes needed for the same percentage decay in the reference experiment. For the creatinine, FIG. 18 shows that the apparatus according to the invention only takes 80 minutes for a 30% decay, while the apparatus without a pressure-varying means takes 120 minutes for the same decay. These facts show that the time needed for therapy can be greatly shortened.

Figure 19:
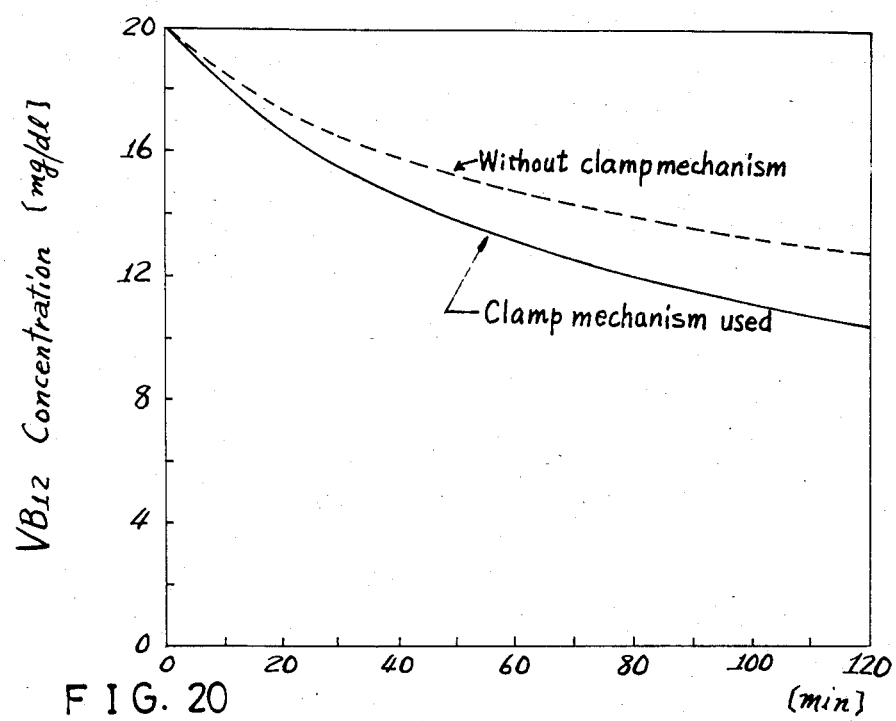
Figure 20:
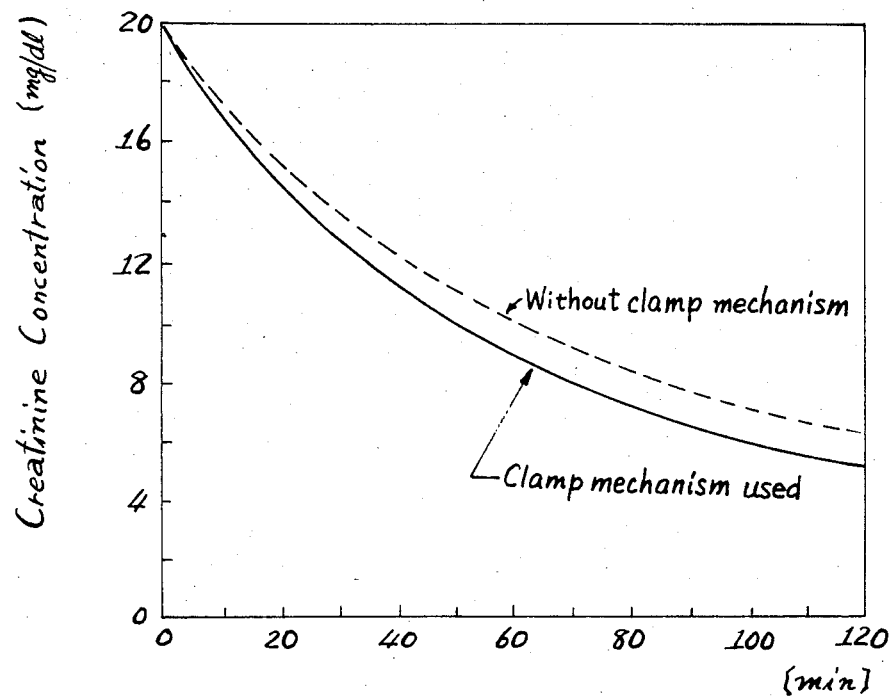

FIGS. 19 and 20 show the results of an experiment performed with the apparatus shown in FIG. 5 modified according to FIG. 10 and using charcoal as a blood treating material. It was confirmed in advance that when fresh bovine blood with a hematocrit value of 35% flows at $QB=100$ ml/min, the maximum filtering rate $Q_{Fmax}$ of the membranes is about 35 ml/min and the pressure $P_{vmax}$ at the outlet 23 is about 35 mmHg. The valve 41, which is a kind of pinch valve, was adjusted so as to repeat throttling of a predetermined degree, being actuated by the electromagnetic means controlled by the timer 42. In this experiment the degree of throttling was adjusted to give an outlet pressure $P_v=35$ mmHg at $QB=65$ ml/min. Under these conditions, the pressure at the outlet rises to 35 mmHg when the valve 41 was throttled, and then the plasma filters into the blood treating material. After the duration of the throttling set on the timer 42 has expired, the pressure is relieved so that the piston 29' acted on by the restoring force of the spring 32' forces the plasma through the membranes 5 into the blood channels 24 from the blood treating material containing space.

Under these conditions 2 liters of the fresh bovine blood (with a hematocrit value of 35%) containing both $VB_{12}$ and creatinine at the same concentration of 20 ml/dl was circulated for 2 hours at QB=100 ml/min and adsorption was performed by the charcoal. A reference experiment was also performed both for $VB_{12}$ and for creatinine but using no pressure varying means.

FIGS. 19 and 20 show the result for $VB_{12}$ and for creatinine, respectively, the solid lines showing the results of the apparatus according to the invention and the dotted lines the results of the reference experiment performed without a pressure-varying means. The times for reaching the levels of $VB_{12}$ and creatinine are substantially the same as for FIGS. 17 and 18.

CONCLUSION

The apparatus of the present invention, which can be made in a compact form, has a wide range of applications, and can be furnished with an apparatus for quantitatively removing fluid or for quantitatively substituting fluid. In addition the present invention can be clinically applied as a useful therapeutical means for a patient suffering from acute hepatic insufficiency, immunological diseases or drug intoxication by using charcoal, immobilized enzymes, immunoadsorbents or other various adsorbents as the blood treating material.

What is claimed is:

1. An apparatus for blood treatment, comprising:
a housing having a blood inlet means for introducing blood to be treated and a blood outlet means for exhausting treated blood from said housing;
at least one blood channel within said housing and extending from said inlet means to said outlet means and being constituted by a plasma-separating membrane capable of allowing plasma component of blood to permeate therethrough while preventing blood cells from penetrating therethrough, said housing having a space therein surrounding said membrane;
a blood treating material packed in said space within said housing around said membrane;
a pump connected to said inlet means for pumping the blood to be treated into said inlet means at a predetermined pressure;
a blood circuit connected to said outlet means;
at least part of the housing comprising means including an elastic material in contact with said blood treating material for undergoing elastic expansion in response to a pressure buildup and for undergoing contraction when said pressure is reduced; and
a clamp mechanism downstream of said outlet means including means for intermittently operating said clamp mechanism for clamping said blood circuit for at least substantially reducing flow of blood through said blood circuit downstream of said outlet means and for causing a buildup of pressure in said at least one blood channel for causing plasma component of blood flowing in said at least one blood channel to permeate through said plasma-separating membrane toward said blood treating material to bring plasma into contact with said blood treating material and building up pressure in said space around said membrane and causing elastic expansion of said elastic material, then for releasing said blood circuit for allowing reduction of pressure in said blood circuit, and for permitting said elastic material to contract for exerting a force on plasma and blood treating material in said space for forcing plasma back through said plasma separating membrane back into said at least one blood channel.

2. An apparatus as claimed in claim 1 wherein said housing has an enclosure within said housing enclosing said space and at least part of which enclosure is said elastic material, and said housing has a further space therein around said enclosure, and an elastic packing material filling said further space around said enclosure.

3. An apparatus as claimed in claim 1 wherein said clamp mechanism includes a timer means for controlling said intermittent operating of said clamp mechanism.

4. An apparatus as claimed in claim 1 wherein said housing has an enclosure within said housing enclosing said space and at least part of which enclosure is said elastic material, and said housing has a further space therein around said enclosure, and an elastic expansion and contraction means being provided outside said housing, said means consisting of a cylinder connected to said further space, a piston reciprocally slidable in said cylinder, and compressible means acting on said piston to counterbalance pressure of plasma in said space.

5. An apparatus for blood treatment, comprising:
a housing having a blood inlet means for introducing blood to be treated and a blood outlet means for exhausting treated blood from said housing;
at least one blood channel within said housing and extending from said inlet means to said outlet means and being constituted by a plasma-separating membrane capable of allowing plasma component of blood to permeate therethrough while preventing blood cells from penetrating therethrough, said housing having a space therein surrounding said membrane;
a blood treating material packed in said space within said housing around said membrane;
a pump connected to said inlet means for pumping the blood to be treated into said inlet means at a predetermined pressure;
a blood circuit connected to said outlet means;
an elastic expansion and contraction means provided outside said housing, said means consisting of a cylinder connected to said housing opening into said blood treating material-containing space, a piston reciprocally slidable in said cylinder, and compressible means acting on said piston to counterbalance a buildup of pressure of plasma in said blood treating material-containing space;
a clamp mechanism downstream of said outlet means including means for intermittently operating said clamp mechanism for clamping said blood circuit for at least substantially reducing flow of blood through said blood circuit downstream of said outlet means and for causing a buildup of pressure in said at least one blood channel for causing plasma component of blood flowing in said at least one blood channel to permeate through said plasma-separating membrane toward said blood treating material to bring plasma into contact with said blood treating material and building up pressure in said space around said membrane and causing movement of said piston against said compressible means, and then for releasing said blood circuit for allowing reduction of pressure in said blood circuit, and for permitting said compressible means to expand and exert a force on plasma and blood treating material in said space for forcing plasma back through said plasma separating membrane back into said at least one blood channel.

6. An apparatus as claimed in claim 5 in which said compressible means is a spring.

7. An apparatus as claimed in claim 5 in which said compressible means is a compressible gas.

* * * * *